US008855385B2

(12) United States Patent
Kriston et al.

(10) Patent No.: US 8,855,385 B2
(45) Date of Patent: Oct. 7, 2014

(54) APPARATUS AND METHOD FOR MULTI-ENERGY TISSUE QUANTIFICATION

(75) Inventors: Andras Kriston, Mako (HU); Peter Alexander John Lamb, Clifton Park, NY (US); Paulo Ricardo dos Santos Mendonca, Clifton Park, NY (US); Masayuki Kudo, Kanagawa (JP); Kosuke Sasaki, Tokyo (JP); Souma Sengupta, Cupertino, CA (US); Rahul Bhotika, Niskayuna, NY (US); Laszlo Rusko, Szeged (HU); Bipul Das, Bangalore (IN); Scott David Wollenweber, Waukesha, WI (US); Ferenc Kovacs, Kecskemet (HU)

(73) Assignee: General Electric Company, Schenectady, NY (US)

(*) Notice: Subject to any disclaimer, the term of this patent is extended or adjusted under 35 U.S.C. 154(b) by 245 days.

(21) Appl. No.: 13/542,964

(22) Filed: Jul. 6, 2012

(65) Prior Publication Data
US 2014/0010427 A1    Jan. 9, 2014

(51) Int. Cl.
*G06K 9/00* (2006.01)
(52) U.S. Cl.
USPC ................................ 382/128; 128/922; 378/4
(58) Field of Classification Search
USPC ........ 382/128, 130, 131, 132, 133; 378/4–27, 378/44–50, 87, 88, 89, 91, 101, 145, 148, 378/150; 128/922; 250/370.08, 370.09, 250/390.07, 390.1, 393, 394, 493.1–503.1
See application file for complete search history.

(56) References Cited

U.S. PATENT DOCUMENTS

| 6,836,528 | B2 * | 12/2004 | Reddy et al. | 378/5 |
| 6,999,549 | B2 | 2/2006 | Sabol et al. | |
| 7,058,155 | B2 * | 6/2006 | Piacsek et al. | 378/4 |
| 7,190,757 | B2 * | 3/2007 | Ying et al. | 378/5 |
| 7,236,559 | B2 * | 6/2007 | Jha et al. | 378/5 |
| 7,724,865 | B2 * | 5/2010 | Wu et al. | 378/5 |
| 7,778,454 | B2 * | 8/2010 | Grasruck et al. | 382/128 |
| 7,995,702 | B2 * | 8/2011 | Xu et al. | 378/4 |

(Continued)

OTHER PUBLICATIONS

Davidson et al., "Protocol for measurement of liver fat by computed tomography," Journal of Applied Physiology, vol. 100, pp. 864-868, 2006; First published Nov. 17, 2005.

(Continued)

*Primary Examiner* — Anand Bhatnagar
(74) *Attorney, Agent, or Firm* — Ziolkowski Patent Solutions Group, SC

(57) ABSTRACT

An apparatus for multi-energy tissue quantification includes an x-ray imaging system comprises an x-ray source configured to emit a beam of x-rays toward an object to be imaged, a detector configured to receive the x-rays attenuated by the object, and a data acquisition system (DAS) operably coupled to the detector. A computer operably connected to the x-ray source and the DAS is programmed to cause the x-ray source to emit x-rays at each of a first kVp and a second kVp toward the detector, acquire x-ray data from x-rays emitted at the first and second kVp through a region of interest (ROI), and perform a first multi-material decomposition based on the acquired x-ray data. The computer is also programmed to quantify a volume fraction of a first material in the ROI based on the first multi-material decomposition and display the volume fraction of the first material to a user.

21 Claims, 5 Drawing Sheets

(56) References Cited

U.S. PATENT DOCUMENTS

| | | | | |
|---|---|---|---|---|
| 8,055,039 | B2* | 11/2011 | Wu et al. | 382/128 |
| 8,290,232 | B2* | 10/2012 | Liu et al. | 382/131 |
| 8,311,182 | B2* | 11/2012 | Chandra et al. | 378/5 |
| 8,315,352 | B2* | 11/2012 | Wu et al. | 378/5 |
| 8,363,917 | B2* | 1/2013 | Fan et al. | 382/131 |
| 8,611,624 | B2* | 12/2013 | Poonawalla et al. | 382/128 |
| 2004/0264626 | A1* | 12/2004 | Besson | 378/4 |
| 2004/0264627 | A1* | 12/2004 | Besson | 378/5 |
| 2005/0147201 | A1* | 7/2005 | Hoffman | 378/15 |
| 2006/0251209 | A1 | 11/2006 | Tkaczyk et al. | |
| 2009/0052612 | A1* | 2/2009 | Wu et al. | 378/5 |
| 2009/0080597 | A1* | 3/2009 | Basu | 378/5 |

OTHER PUBLICATIONS

Patel et al., "Recent advances in imaging hepatic fibrosis and steatosis," Expert Reviews, Expert Rev. Gastroenterol. Hepatol. 5(1), pp. 91-104, 2011.

Kriston et al., "Liver Fat Quantification Using Fast kVp-Switching Dual Energy CT," Proc. SPIE 7962, 79623W, pp. 1-8, 2011.

Bydder et al., "Assessment of liver fat quantification in the presence of iron," ScienceDirect, Magnetic Resonance Imaging, vol. 28, pp. 767-776, 2010.

Reeder et al., "Quantification of Liver Fat with Magnetic Resonance Imaging," Magn Reson Imaging Clin N Am 18, pp. 337-357, 2010.

Schwenzer et al., "Non-invasive assessment and quantification of liver steatosis by ultrasound, computed tomography and magnetic resonance," Journal of Hepatology, vol. 51, pp. 433-445, 2009.

Hijona et al., "Accurate fat fraction quantification by multiecho gradient-recalled-echo magnetic resonance at 1.5 T in rats with nonalcoholic fatty liver disease," European Journal of Radiology, vol. 81, pp. 1122-1127, 2012.

Schuchmann et al., "Non-invasive quantification of hepatic fat fraction by fast 1.0, 1.5 and 3.0 T MR imaging," European Journal of Radiology, vol. 62, pp. 416-422, 2007.

d'Assignies et al., "Simultaneous assessment of liver volume and whole liver fat content: a step towards one-stop shop preoperative MRI protocol," Eur Radiol, vol. 21, pp. 301-309, 2011.

Guiu et al, "Mapping of liver fat with triple-echo gradient echo imaging: validation against 3.0-T proton MR spectroscopy," Eur Radiol, vol. 19, pp. 1786-1793, 2009.

Mendonca et al., "Multi-Material Decomposition of Spectral CT Images," Proc. of SPIE, vol. 7622, pp. 76221W-1-76221W-9, 2010.

\* cited by examiner

APPARATUS AND METHOD FOR MULTI-ENERGY TISSUE QUANTIFICATION

BACKGROUND

Embodiments of the present invention relate generally to diagnostic imaging and, more particularly, to an apparatus and method for multi-energy tissue quantification of one or more tissues-of-interest.

Medical imaging devices comprise x-ray systems, magnetic resonance (MR) systems, ultrasound systems, computed tomography (CT) systems, positron emission tomography (PET) systems, ultrasound, nuclear medicine, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction. Such typical systems, however, do not include an ability to discriminate spectral energy content of x-rays as they pass through an object being imaged.

However, as known in the art, multi-energy spectral CT systems have been developed that can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. Different approaches have been developed to realize dual energy or spectral imaging. To name a few, dual x-ray source and detector, a single x-ray source with an energy discriminative detector, and a single x-ray source and detector with multiple acquisitions at different kVp or interleaved with fast kVp switching capability are examples of techniques.

In a dual x-ray source and detector system, typically two x-ray sources are provided, each having a respective detector positioned opposite thereto such that x-rays may be emitted from each source having a different spectral energy content. Thus, based on the known energy difference of the sources, a scintillating or energy integrating device may suffice to distinguish energy content and different materials within the object being imaged.

In a single x-ray source with an energy discriminative detector, energy sensitive detectors may be used such that each x-ray photon reaching the detector is recorded with its photon energy. Such systems may use a direct conversion detector material in lieu of a scintillator.

Accurate quantification of liver fat is important in the diagnosis, characterization, and treatment of fatty liver disease. The early diagnosis of fatty liver disease with associated treatments therefor can help prevent the onset of more serious liver diseases and can even lead to a reverse of some forms of fatty liver disease. Furthermore, concentration of liver fat can be used as a clinical diagnostic for liver resection.

Liver biopsy is a technique used for liver-fat quantification, but biopsy results may be subject to dispute due to sampling error. In addition, a liver biopsy requires an invasive procedure to obtain a tissue sample on which to perform the biopsy.

Non-invasive imaging with magnetic resonance (MR), ultrasound (US), and computed tomography (CT) scanners are of increasing interest and acceptance. Of these three modalities, MR is most often cited as the superior modality for liver-fat quantification since it offers several methods for direct and accurate liver-fat quantification. However, alternatives to MR are desired since MR scanning is costly and time-consuming.

Many techniques currently exist for the quantification of liver fat with CT, and all rely on the inverse relationship between liver fat content and liver attenuation. A first technique involves direct measurement of liver attenuation of values in Hounsfield units (HU). Second and third techniques normalize the average HU value of the liver by that of the spleen, and either involve computing differences (liver minus spleen) or ratios (typically, spleen to liver). However, these techniques are semi-quantitative and infer concentration of liver fat heuristically.

One limitation of these CT techniques is that they are impractical for iodinated contrast-enhanced CT acquisitions, where the presence of iodinated contrast agents greatly skews HU values. This variability depends on which contrast agent was administered, patient-specific absorption rates of contrast media, and contrast-enhanced phase of imaging (arterial, portal venous, delayed). Furthermore, HU values of the liver and spleen are often obtained through the use of 2D regions of interest (ROIs), which may lead to placement and registration error, and may not be representative of the whole liver. While dual-energy CT (DECT) may overcome a contrast-enhanced limitation via material decomposition, existing methods still rely on HU values and thus remain semi-quantitative in nature.

Therefore, it would be desirable to have a system and method of fat quantification that overcome the aforementioned drawbacks.

BRIEF DESCRIPTION

According to an aspect of the invention, an x-ray imaging system comprises an x-ray source configured to emit a beam of x-rays toward an object to be imaged, a detector configured to receive the x-rays attenuated by the object, and a data acquisition system (DAS) operably coupled to the detector. A computer operably connected to the x-ray source and the DAS is programmed to cause the x-ray source to emit x-rays at each of a first kVp and a second kVp toward the detector, acquire x-ray data from x-rays emitted at the first and second kVp through a region of interest (ROI), and perform a first multi-material decomposition based on the acquired x-ray data. The computer is also programmed to quantify a volume fraction of a first material in the ROI based on the first multi-material decomposition and display the volume fraction of the first material to a user.

According to another aspect of the invention, a method of x-ray imaging comprises acquiring x-ray data emitted through a region of interest (ROI) from an x-ray source at multiple kVp levels and decomposing a plurality of materials within the ROI based on the acquired x-ray data. The method also comprises quantifying a volume fraction of a first material of the plurality of materials within the ROI and displaying the quantified volume fraction.

According to yet another aspect of the invention, a computer readable storage medium has stored thereon a computer program comprising instructions, which, when executed by a computer, cause the computer to acquire x-ray data emitted through a region of interest (ROI) from an x-ray source at multiple kVp levels and decompose a plurality of materials within the ROI based on the acquired x-ray data. The instructions further cause the computer to quantify a volume fraction of a first material of the plurality of materials within the ROI and display the quantified volume fraction.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

The operating environment of the present invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
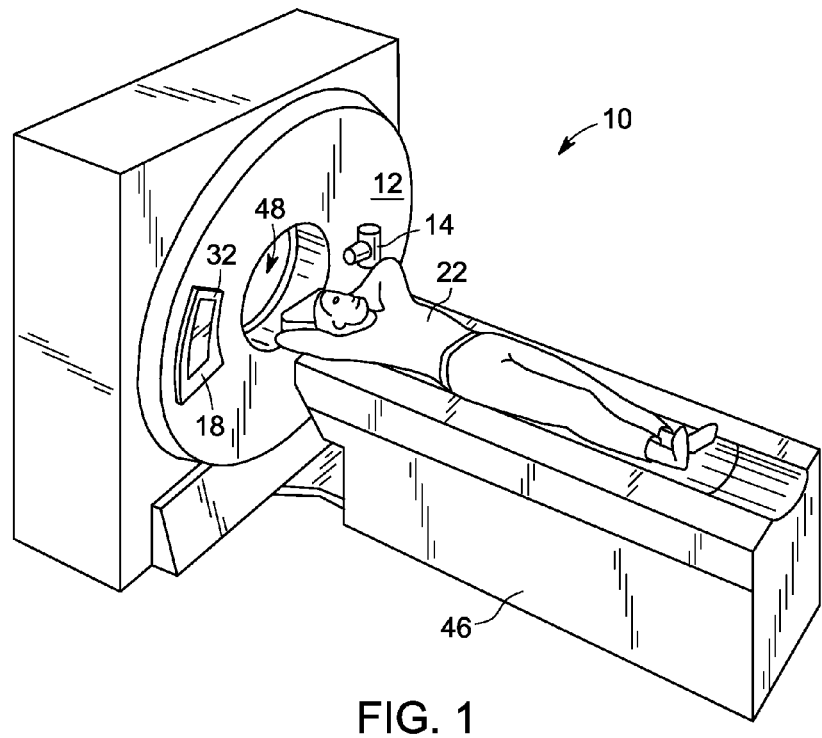
FIG. 1 is a pictorial view of a CT imaging system.
Figure 2:
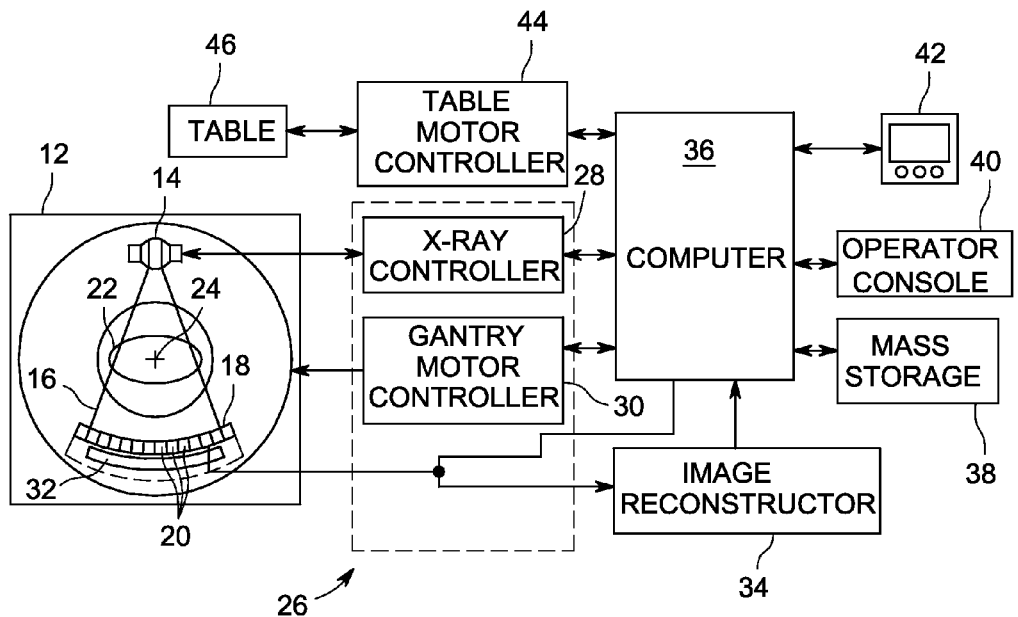
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 through a dynamically controlled multi-position spectral filter 17 and toward a detector assembly or collimator 18 on the opposite side of the gantry 12. The beam of x-rays 16 generated by x-ray source 14 is collimated to desired dimensions by a pre-patient collimator 19, such as by using tungsten blades in front of the x-ray source and different detector apertures, so as to define the size and shape of the beam of x-rays 16 that emerges from the x-ray source 14.

As shown in FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing, with the processed data commonly referred to as projection data or projections. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12, the operation of x-ray source 14, and the operation of multi-position spectral filter 17 are governed by a control mechanism 26 of CT system 10. Control mechanism 26 includes an x-ray controller 28 that provides power and timing signals to an x-ray source 14, a gantry motor controller 30 that controls the rotational speed and position of gantry 12, and a filter controller 31 that controls a positioning of a filter element in the spectral filter 17. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
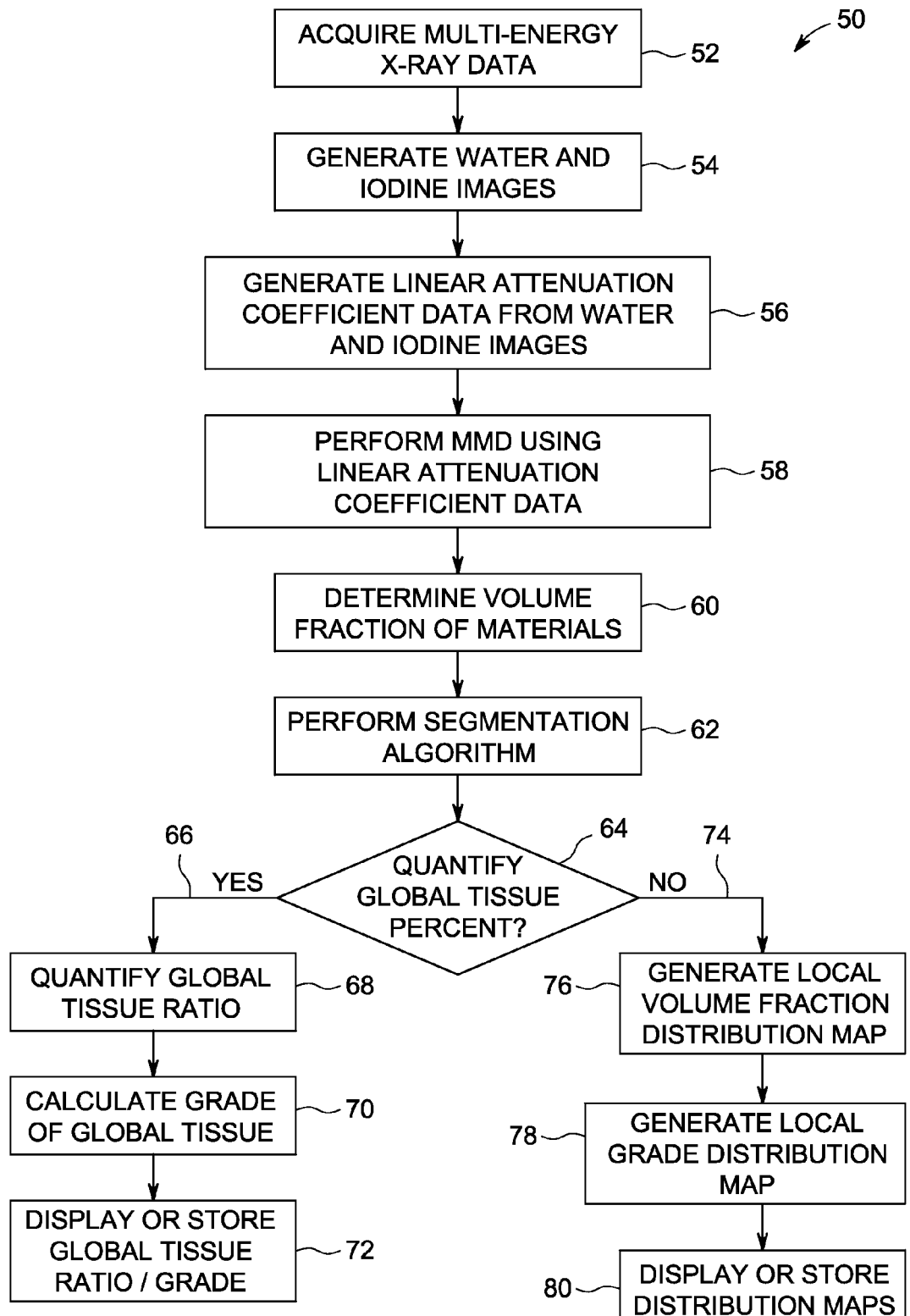
FIG. 3 is an illustration of a technique for quantifying a volume fraction of a tissue according to an embodiment of the invention.

Referring to FIG. 3, a technique 50 for quantifying one or more materials in a tissue- or organ-of-interest is illustrated according to one embodiment of the invention. Technique 50 includes acquiring 2D or 3D multi-energy x-ray data at block 52 from a region of interest (ROI) of an imaging subject. According to one embodiment, CT system 10 is employed for multi-energy imaging. In another embodiment, another x-ray system (not shown) may be used.

In multi-energy imaging, two or more sets of projection data are typically obtained for an imaged subject/object at different tube peak kilovoltage (kVp) levels, which change the peak and spectrum of energy of the incident photons comprising the emitted x-ray beams. That is, x-ray source 14 is operated at two or more different tube kVp levels. In one example, low and high kVp spectra are respectively 70 kV and 140 kV, and in one example, the low kVp potential and the high kVp potential are each for a period less than one millisecond for fast kVp switching. However, it is to be understood that any low and high kVp spectra may be selected for multi-energy imaging, according to the invention. It is also to be understood that one millisecond duration at low and high kVp potentials is an example, and that any length period may be implemented, depending on imaging application, according to the invention. That is, for slow kVp switching in an example, a complete set of data at a low kVp may be acquired before the acquisition of the complete set of data at a high kVp and vice-versa. Other well-known techniques for acquiring the multi-level data are also contemplated.

At block 54, an algorithm is performed on the acquired sets of projection data to generate a water image and an iodine image therefrom. The water and iodine images are converted at block 56 to sets of data in the linear attenuation coefficient space, and at block 58, a multi-material decomposition algorithm is performed using the linear attenuation coefficient data to separate target materials from one another in the ROI into respective datasets. For example, during MMD, sets of data in the linear attenuation coefficient space may be used to generate a first dataset for fat and a second dataset for soft tissue in the ROI. It is contemplated, however, that other datasets may also be created for other materials. The linear attenuation coefficient space datasets are used to determine the volume fractions of the materials in each voxel at block 60. For example, the percent of fat and the percent of soft tissue in each voxel may be determined.

While technique 50 may be performed on the entire ROI, it may be desirable to limit or reduce the amount of data stored or shown to a user. Accordingly, as shown in block 62, a segmentation algorithm may be performed to isolate a particular area or section within the ROI. According to an embodiment of the invention, the segmentation may be automatic to segment a predetermined tissue type or organ. For example, the segmentation may automatically segment the voxels corresponding with a predetermined organ such as the liver. In a semi-automatic embodiment, a user may choose the tissue or organ on the fly. In a manual embodiment, an image of the ROI may be shown to a user, and the user may be allowed to select or draw a region containing the tissue or organ of interest. The segmentation algorithm, whether automatic, semi-automatic or manual, masks non-segmented data such that the volume fraction data remaining in the distribution map corresponds only with the segmented region. It is contemplated that segmentation at block 62 may be performed earlier in technique 50 than that shown in FIG. 3. For example, segmentation may be performed prior to performing the MMD algorithm at block 58.

For quantifying a tissue percent (e.g., such as fat) based on the volume fraction of materials in the entire ROI or in a segmented part thereof, technique 50 determines 64 whether to quantify a global tissue percent. If so 66, the ratio of one or more materials in the entire ROI or segmented part is globally quantified at block 68. At block 70, a grade of the global tissue in the entire ROI or segmented part is calculated. The grading of the tissue may be based on an industry-standard scale or map such as, in one embodiment, a steatosis score. For example, if the percent of fat in a liver is less than five percent, a grade of zero (e.g., healthy) may be calculated. If the percent of fat in the liver is greater or equal to five percent and less than or equal to thirty-three percent, a grade of one (e.g., low fat) may be calculated. For a percent of fat in the liver greater than thirty-three percent but less than or equal to sixty-six percent, a grade of two (e.g., moderate fat) may be calculated. For a percent of liver fat above sixty-six percent, a grade of three (e.g., very fatty) may be calculated. It is contemplated, however, that other grading systems may be used. At block 72, the global tissue ratio and/or the grade may be displayed to a user or stored in a computer readable storage medium.

If a global tissue percent is not quantified 74, a local volume fraction distribution map of a tissue is generated using the volume fractions at block 76. A local grade distribution map of the tissue is generated at block 78. The distribution maps generated at blocks 76, 78, whether corresponding with the entire ROI or with a segmented part, may be shown to a user or stored in a computer readable storage medium at block 80.

The displays at blocks 72, 80 may include 3D volumetric displays or slice-by-slice 2D displays. The displays may be illustrated together with an anatomical image reconstruction of the corresponding region, and the displays may be color-coded on top of the anatomy. In addition, the displays may include scatter or histogram plots of the calculated data.

Figure 4:
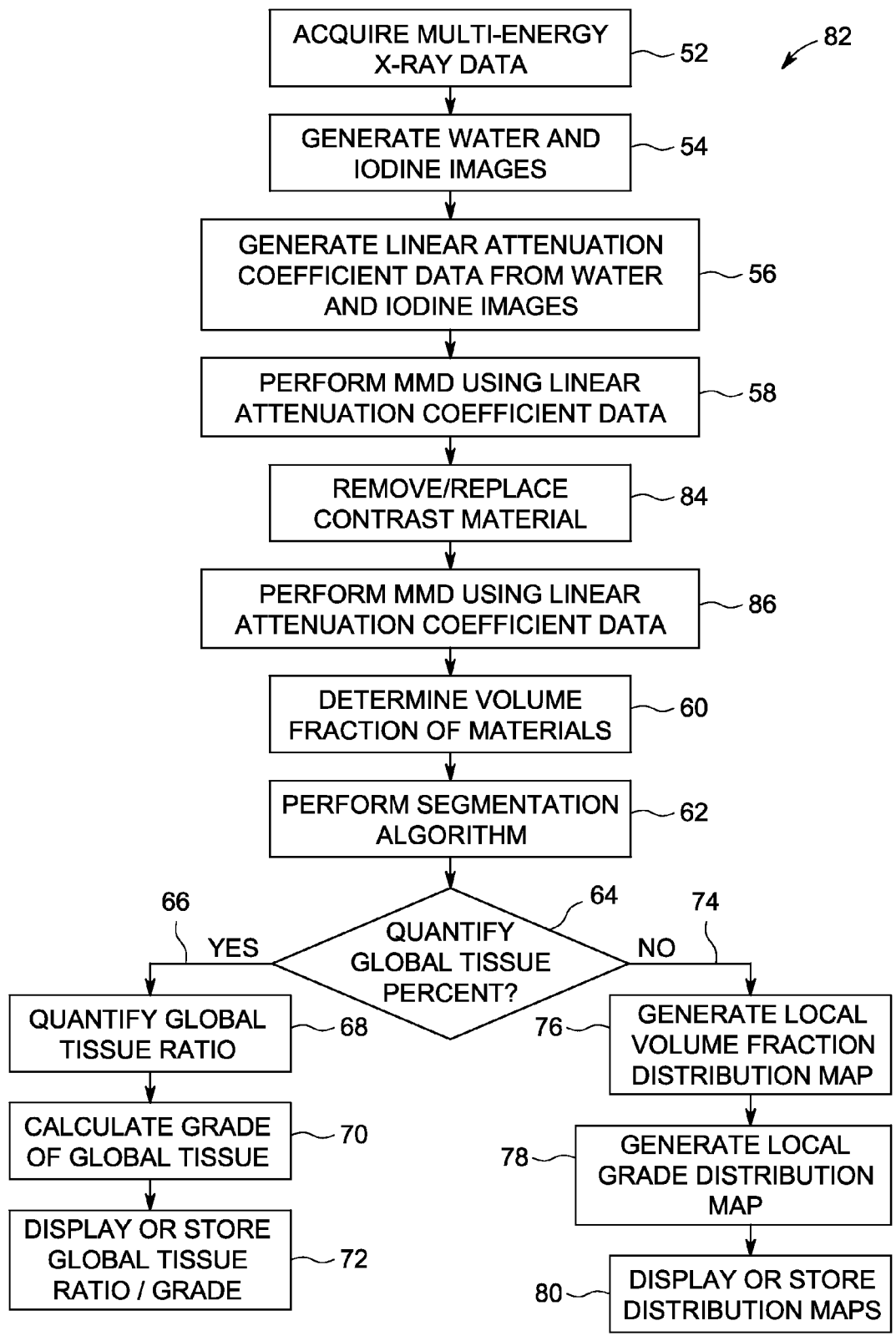
FIG. 4 is an illustration of a technique for quantifying a volume fraction of a tissue according to another embodiment of the invention.

FIG. 4 illustrates a technique 82 incorporating the steps of technique 50 of FIG. 3 together with steps for removing contrast when the multi-energy x-ray data is acquired in the presence of an iodinated contrast agent. Steps in common with technique 50 have been described above.

To remove the contrast material from the data on which the MMD of block 58 is performed, a first MMD is performed at block 84 using the linear attenuation coefficient data to separate at least the contrast material and blood from other tissues in the ROI. At block 86, the contrast material data is removed or replaced by blood data to remove the contrast material from the linear attenuation coefficient datasets. Thereafter, steps 60-80 are performed as described above.

Figure 5:
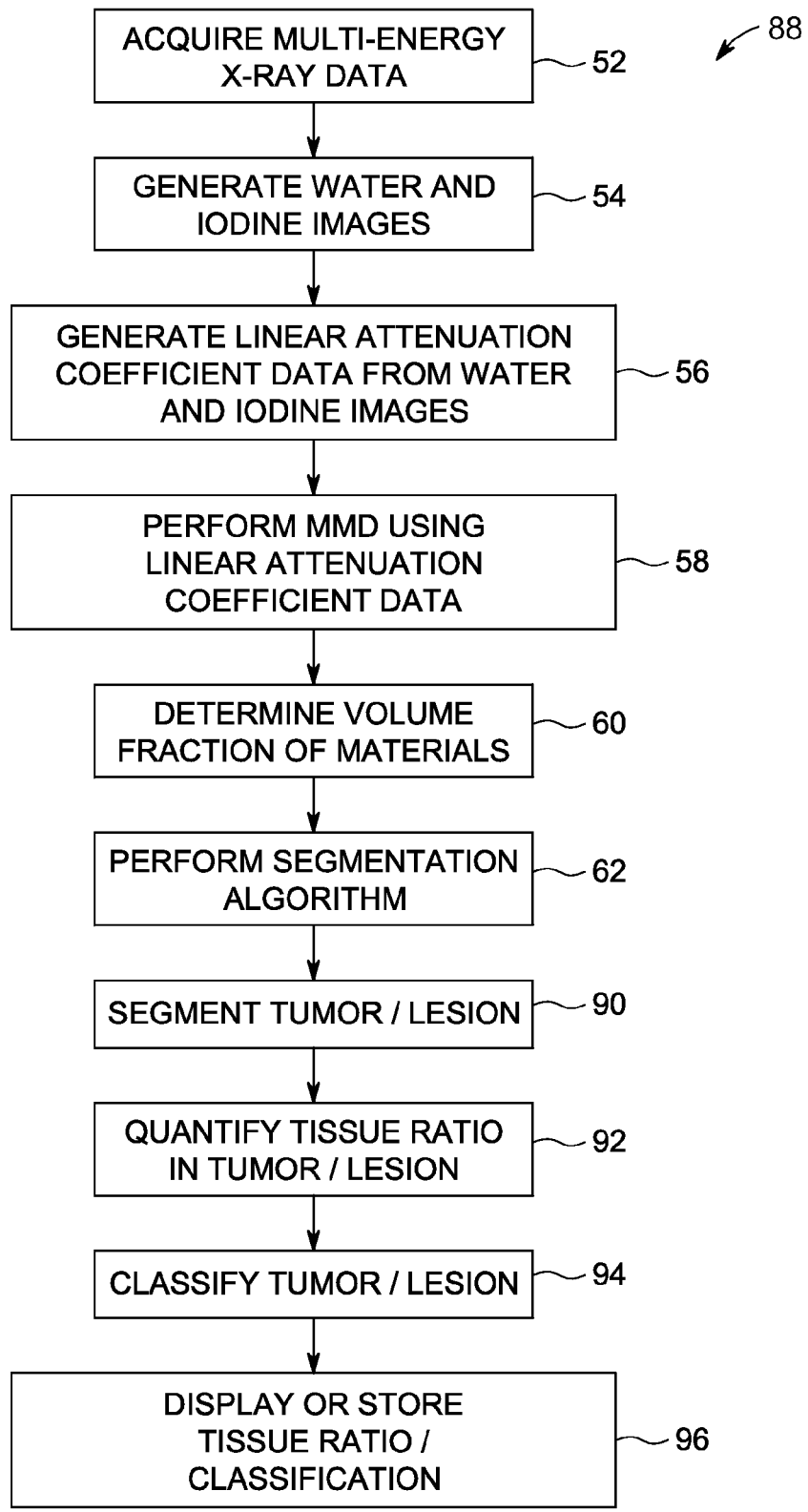
FIG. 5 is an illustration of a technique for quantifying a volume fraction of a tissue according to another embodiment of the invention.

FIG. 5 illustrates a technique 88 for classifying a tumor or lesion according to an embodiment of the invention. Technique 88 incorporates steps 52-62 of technique 50 of FIG. 3, which have been described above.

At block 90, a tumor or lesion is segmented from the ROI. The tumor/lesion segmentation may be automatically determined based on the multi-material decomposition or may be semi-automatically or manually determined based on user input. A tissue ratio (e.g., fat ratio) of the region of the ROI segmented to contain the tumor/lesion is quantified at block 92, the tissue ratio is used to classify the tumor/lesion. A classification algorithm may select the type of tumor/lesion based on the tissue data quantified at block 94. For example, the amount of fat in a lesion may be used to classify the lesion according to a comparison with fat levels in known lesion types. The tissue ratio and/or classification of the tumor/lesion may be shown to a user or stored in a computer readable storage medium at block 96.

Figure 6:
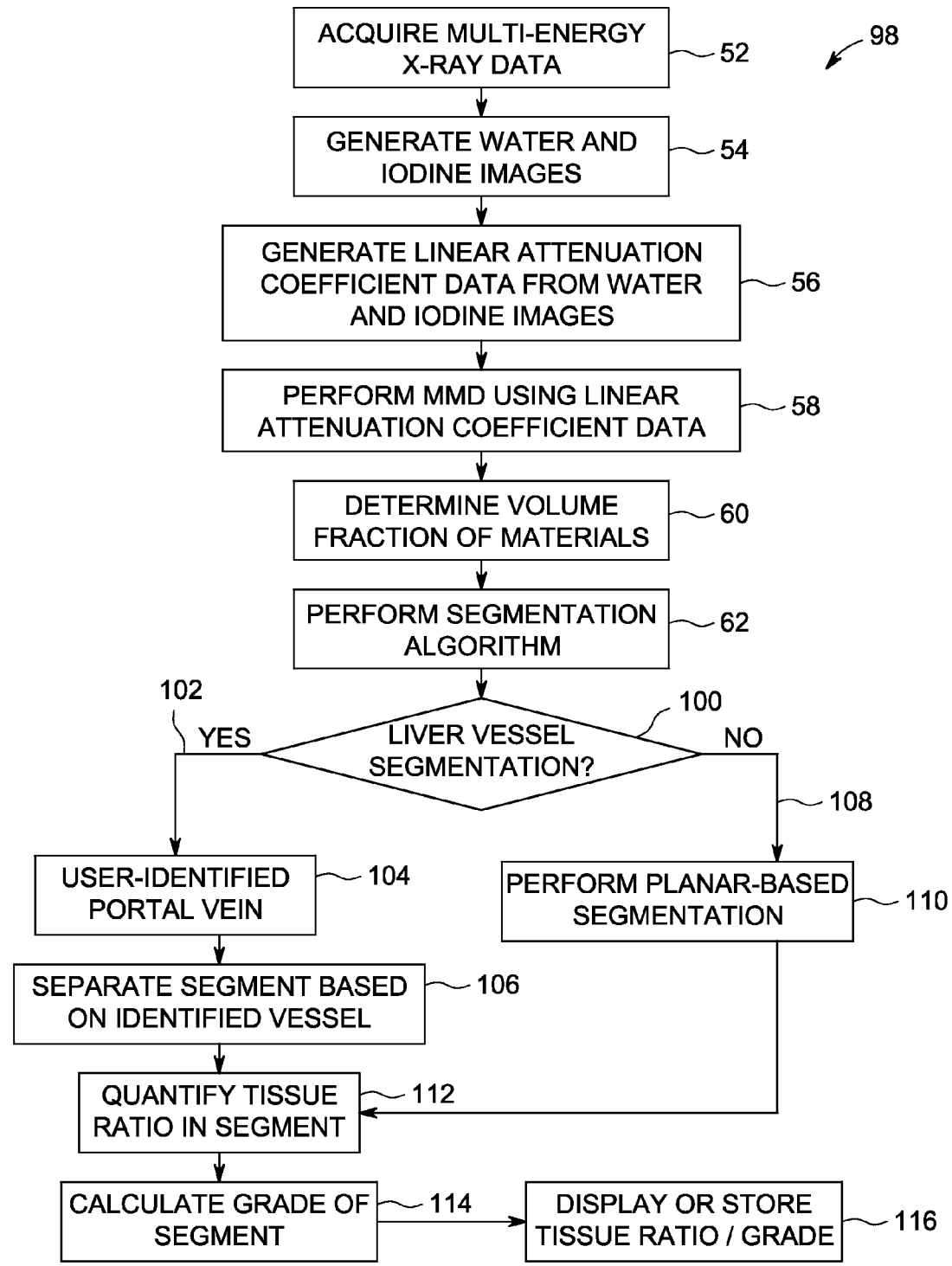
FIG. 6 is an illustration of a technique for quantifying a volume fraction of a tissue according to another embodiment of the invention.

FIG. 6 illustrates a technique 98 for quantifying a tissue ratio in a liver segment according to an embodiment of the invention. Technique 98 incorporates steps 52-62 of technique 50 of FIG. 3, which have been described above.

Technique 98 includes segmenting the liver into one or more of the liver Couinaud segments. Similarly, lobes of the liver may be segmented in a like manner. Such segmentation may be semi-automatically based on identification of the portal vein or may be semi-automatically performed based on planar-based segmentation. Accordingly, technique 98 determines 100 whether to identify the one or more Couinaud segments via a liver vessel segmentation technique. If so 102, a user identifies a region of a liver vessel (e.g., the portal vein or other hepatic artery or vein) on an anatomical image of the liver at block 104. Based on the user-identified liver vessel region, the desired one or more Couinaud segments of the liver are automatically separated or segmented from the rest at block 106. Alternatively, the segmentation may be fully manual in which the user identifies the entire Couinaud segment. If a planar-based segmentation is to be performed block 108, block 110 allows a user to select or define the desired one or more Couinaud segments based on anatomical images displayed to the user. In one embodiment, a virtual scalpel technique may be used.

When the desired one or more Couinaud segments have been identified and segmented, a tissue ratio (e.g., fat ratio) of the Couinaud segment(s) is quantified at block 112. At block 114, a grade of the tissue of the Couinaud segment(s) is calculated. The grading of the tissue may be based on an industry-standard scale or map such as, in one embodiment, a steatosis score as described above. At block 116, the tissue ratio and/or the tissue grade of the Couinaud segment(s) may be displayed to a user or stored in a computer readable storage medium.

A technical contribution for the disclosed method and apparatus is that it provides for a computer implemented apparatus and method for multi-energy tissue quantification of one or more tissues-of-interest.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to an embodiment of the invention, an x-ray imaging system comprises an x-ray source configured to emit a beam of x-rays toward an object to be imaged, a detector configured to receive the x-rays attenuated by the object, and a data acquisition system (DAS) operably coupled to the detector. A computer operably connected to the x-ray source and the DAS is programmed to cause the x-ray source to emit x-rays at each of a first kVp and a second kVp toward the detector, acquire x-ray data from x-rays emitted at the first and second kVp through a region of interest (ROI), and perform a first multi-material decomposition based on the acquired x-ray data. The computer is also programmed to quantify a volume fraction of a first material in the ROI based on the first multi-material decomposition and display the volume fraction of the first material to a user.

According to another embodiment of the invention, a method of x-ray imaging comprises acquiring x-ray data emitted through a region of interest (ROI) from an x-ray source at multiple kVp levels and decomposing a plurality of materials within the ROI based on the acquired x-ray data. The method also comprises quantifying a volume fraction of a first material of the plurality of materials within the ROI and displaying the quantified volume fraction.

According to yet another embodiment of the invention, a computer readable storage medium has stored thereon a computer program comprising instructions, which, when executed by a computer, cause the computer to acquire x-ray data emitted through a region of interest (ROI) from an x-ray source at multiple kVp levels and decompose a plurality of materials within the ROI based on the acquired x-ray data. The instructions further cause the computer to quantify a volume fraction of a first material of the plurality of materials within the ROI and display the quantified volume fraction.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An x-ray imaging system comprising:
an x-ray source configured to emit a beam of x-rays toward an object to be imaged;
a detector configured to receive the x-rays attenuated by the object;
a data acquisition system (DAS) operably coupled to the detector; and
a computer operably connected to the x-ray source and the DAS, the computer being programmed to:
cause the x-ray source to emit x-rays at each of a first kVp and a second kVp toward the detector;
acquire x-ray data from x-rays emitted at the first and second kVp through a region of interest (ROI);
perform a first multi-material decomposition based on the acquired x-ray data;
quantify a volume fraction of a first material in the ROI based on the first multi-material decomposition;
display the volume fraction of the first material to a user; and
grade an object of interest within the ROI based on the volume fraction of the first material;
wherein the computer, in being programmed to grade the object of interest, is programmed to:
determine a percentage of fat within the object of interest; and
apply a steatosis score to the object of interest based on the percentage of fat.

2. The x-ray imaging system of claim 1 wherein the computer, in being programmed to quantify the volume fraction, is programmed to quantify the volume fraction of a global amount of the first material in an object of interest within the ROI.

3. The x-ray imaging system of claim 2 wherein the object of interest comprises an organ.

4. The x-ray imaging system of claim 3 wherein the organ comprises a liver.

5. The x-ray imaging system of claim 2 wherein the first material comprises fat.

6. The CT imaging system of claim 1 wherein the computer is further programmed to:
segment a sub-region within the ROI; and
mask volume fraction data of the first material outside of the sub-region.

7. The CT imaging system of claim 6 wherein the computer, in being programmed to segment the sub-region, is programmed to segment a Couinaud segment of a liver.

8. The CT imaging system of claim 6 wherein the computer is further programmed to segment the sub-region prior to performing the first multi-material decomposition.

9. The CT imaging system of claim 1 wherein the computer is further programmed to:
perform a second multi-material decomposition based on the acquired x-ray data;
identify a contrast material based on the second multi-material decomposition; and
perform the first multi-material decomposition based on a removal of the contrast material.

10. The CT imaging system of claim 1 wherein the computer is further programmed to:
segment a tumor or lesion within the ROI;
quantify the volume fraction of the first material in the tumor or lesion; and
classify the tumor or lesion based on the quantified volume fraction of the first material.

11. A method of x-ray imaging comprising:
acquiring x-ray data emitted through a region of interest (ROI) from an x-ray source at multiple kVp levels;
decomposing a plurality of materials within the ROI based on the acquired x-ray data;
quantifying a volume fraction of a first material of the plurality of materials within the ROI; and
displaying the quantified volume fraction;
isolate at least one Couinaud segment of a liver within the ROI; and
calculate a grade of the at least one Couinaud segment based on the quantified volume fraction of the first material therein, wherein the first material comprises fat.

12. The method of claim 11 wherein quantifying comprises quantifying a global volume fraction of the first material in an object within the ROI or quantifying a local volume fraction of the first material within each voxel of the object within the ROI.

13. The method of claim 12 wherein the method further comprises grading the object based on the global volume fraction or the local volume fraction.

14. The method of claim 11 wherein the method further comprises segmenting a first segment of an object within the ROI from a second segment of the object.

15. A non-transitory computer readable storage medium having stored thereon a computer program comprising instructions, which, when executed by a computer, cause the computer to:
acquire x-ray data emitted through a region of interest (ROI) from an x-ray source at multiple kVp levels;
decompose a plurality of materials within the ROI based on the acquired x-ray data;
quantify a volume fraction of a first material of the plurality of materials within the ROI;
display the quantified volume fraction;
isolate at least one Couinaud segment of a liver within the ROI; and
calculate a grade of the at least one Couinaud segment based on the quantified volume fraction of the first material therein, wherein the first material comprises fat.

16. The non-transitory computer readable storage medium of claim 15 wherein the instructions that cause the computer to quantify cause the computer to quantify a global volume fraction of the first material in an object within the ROI or quantifying a local volume fraction of the first material within each voxel of the object within the ROI.

17. The non-transitory computer readable storage medium of claim 16 wherein the instructions further cause the computer to:
identify a tumor or lesion within an object of interest within the ROI; and
classify the tumor or lesion based on the quantified volume fraction of the first material within the tumor or lesion.

18. An x-ray imaging system comprising:
an x-ray source configured to emit a beam of x-rays toward an object to be imaged;
a detector configured to receive the x-rays attenuated by the object;
a data acquisition system (DAS) operably coupled to the detector; and
a computer operably connected to the x-ray source and the DAS, the computer being programmed to:
cause the x-ray source to emit x-rays at each of a first kVp and a second kVp toward the detector;
acquire x-ray data from x-rays emitted at the first and second kVp through a region of interest (ROI);
perform a first multi-material decomposition based on the acquired x-ray data;
quantify a volume fraction of a first material in the ROI based on the first multi-material decomposition; and
display the volume fraction of the first material to a user;
wherein the computer is further programmed to:
segment a sub-region within the ROI; and
mask volume fraction data of the first material outside of the sub-region.

19. An x-ray imaging system comprising:
an x-ray source configured to emit a beam of x-rays toward an object to be imaged;
a detector configured to receive the x-rays attenuated by the object;
a data acquisition system (DAS) operably coupled to the detector; and
a computer operably connected to the x-ray source and the DAS, the computer being programmed to:
cause the x-ray source to emit x-rays at each of a first kVp and a second kVp toward the detector;
acquire x-ray data from x-rays emitted at the first and second kVp through a region of interest (ROI);
perform a first multi-material decomposition based on the acquired x-ray data;
quantify a volume fraction of a first material in the ROI based on the first multi-material decomposition; and
display the volume fraction of the first material to a user;
wherein the computer is further programmed to:
perform a second multi-material decomposition based on the acquired x-ray data;
identify a contrast material based on the second multi-material decomposition; and
perform the first multi-material decomposition based on a removal of the contrast material.

20. An x-ray imaging system comprising:
an x-ray source configured to emit a beam of x-rays toward an object to be imaged;
a detector configured to receive the x-rays attenuated by the object;
a data acquisition system (DAS) operably coupled to the detector; and a computer operably connected to the x-ray source and the DAS, the computer being programmed to:
cause the x-ray source to emit x-rays at each of a first kVp and a second kVp toward the detector;
acquire x-ray data from x-rays emitted at the first and second kVp through a region of interest (ROI);
perform a first multi-material decomposition based on the acquired x-ray data;
quantify a volume fraction of a first material in the ROI based on the first multi-material decomposition; and
display the volume fraction of the first material to a user;
wherein the computer is further programmed to:
segment a tumor or lesion within the ROI;
quantify the volume fraction of the first material in the tumor or lesion; and
classify the tumor or lesion based on the quantified volume fraction of the first material.

21. A non-transitory computer readable storage medium having stored thereon a computer program comprising instructions, which, when executed by a computer, cause the computer to:

acquire x-ray data emitted through a region of interest (ROI) from an x-ray source at multiple kVp levels;

decompose a plurality of materials within the ROI based on the acquired x-ray data;

quantify a volume fraction of a first material of the plurality of materials within the ROI;

display the quantified volume fraction;

identify a tumor or lesion within an object of interest within the ROI; and classify the tumor or lesion based on the quantified volume fraction of the first material within the tumor or lesion;

wherein the instructions that cause the computer to quantify cause the computer to quantify a global volume fraction of the first material in an object within the ROI or quantifying a local volume fraction of the first material within each voxel of the object within the ROI.

* * * * *